United States Patent
Yang (10) Patent No.: US 10,315,990 B2
(45) Date of Patent: Jun. 11, 2019

(54) ISOTHIOCYANATE COMPOUNDS AND ISOTHIOCYANATE XPO1 PROTEIN INHIBITOR DRUGS THEREOF

(71) Applicant: DRIVINGFORCE THERAPEUTICS Co., Ltd., Dalian, Liaoning Province (CN)

(72) Inventor: Yongliang Yang, Dalian (CN)

(73) Assignee: DRIVINGFORCE THERAPEUTICS (CN)

( * ) Notice: Subject to any disclaimer, the term of this patent is extended or adjusted under 35 U.S.C. 154(b) by 0 days.

(21) Appl. No.: 15/550,783

(22) PCT Filed: Feb. 3, 2016

(86) PCT No.: PCT/CN2016/073238
§ 371 (c)(1),
(2) Date: Aug. 13, 2017

(87) PCT Pub. No.: WO2016/127873
PCT Pub. Date: Aug. 18, 2016

(65) Prior Publication Data
US 2018/0029979 A1 Feb. 1, 2018

(30) Foreign Application Priority Data
Feb. 12, 2015 (CN) .......................... 2015 1 0073762

(51) Int. Cl.
| | |
|---|---|
| *A61K 31/26* | (2006.01) |
| *A61K 31/428* | (2006.01) |
| *C07C 331/22* | (2006.01) |
| *C07C 331/24* | (2006.01) |
| *C07D 213/71* | (2006.01) |
| *C07D 215/36* | (2006.01) |
| *C07D 235/28* | (2006.01) |
| *C07D 239/74* | (2006.01) |
| *C07D 257/04* | (2006.01) |
| *C07D 277/76* | (2006.01) |
| *C07D 311/14* | (2006.01) |
| *C07D 295/096* | (2006.01) |

(52) U.S. Cl.
CPC ............ *C07C 331/24* (2013.01); *A61K 31/26* (2013.01); *A61K 31/428* (2013.01); *C07C 331/22* (2013.01); *C07D 213/71* (2013.01); *C07D 215/36* (2013.01); *C07D 235/28* (2013.01); *C07D 239/74* (2013.01); *C07D 257/04* (2013.01); *C07D 277/76* (2013.01); *C07D 295/096* (2013.01); *C07D 311/14* (2013.01); *C07C 2602/10* (2017.05); *C07C 2603/18* (2017.05); *C07C 2603/24* (2017.05); *C07C 2603/28* (2017.05)

(58) Field of Classification Search
CPC combination set(s) only.
See application file for complete search history.

(56) References Cited

FOREIGN PATENT DOCUMENTS

| | | |
|---|---|---|
| CN | 102659651 A | 9/2012 |
| CN | 103159691 A | 8/2016 |

OTHER PUBLICATIONS

Bordwell, F.G. and Mecca, Thomas G.: Nucleophilic Substitutions in Allylic Systems. Further Evidence against the Existence of the Concerted SN2' Mechanism. Contribution from the Department of Chemistry, Northwestern University, Evanston, Illinois 60201.
Bachi, Mario D. and Denenmark, Daniella: Intramolecular Addition of Carbon-Centered Tinthioimidoyl Radicals to Carbon-Carbon Double Bonds. Synthesis of γ- and δ-Thiolactams. Department of Organic Chemistry, The Weizmann Institute of Science, Rehovot, 76100 Israel.

*Primary Examiner* — Valerie Rodriguez-Garcia
(74) *Attorney, Agent, or Firm* — PROI Intellectual Property US (57) ABSTRACT

The present invention provides an isothiocyanate compound and its application. The compound is an aryl-substituted isothiocyanate compound that has a structure of the general formula I. The isothiocyanate compound of the present invention has very good solubility in water, far better inhibitory activity for XPO1 protein than other non-aryl substituted congeneric compounds, little side effects, and good biological safety and bioavailability, and is quite suitable for clinical application. Therefore, the isothiocyanate compound would have tremendous potential market space and economic benefits.

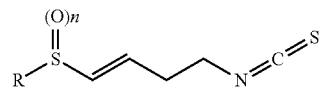

5 Claims, 1 Drawing Sheet

ISOTHIOCYANATE COMPOUNDS AND ISOTHIOCYANATE XPO1 PROTEIN INHIBITOR DRUGS THEREOF

CROSS REFERENCE TO RELATED APPLICATIONS

The present application is the US national stage of International Patent Application PCT/CN2016/073238 filed on Feb. 3, 2016, which, in turn, claims priority to Chinese Patent Application CN 201510073762.9 filed on Feb. 12, 2015.

FIELD OF THE INVENTION

The present invention relates to a novel isothiocyanate XPO1 protein inhibitor and a preparation process and application for the same.

DESCRIPTION OF THE RELATED ART

Some specific proteins in organisms are imported in or exported out of nucleus by specific transport proteins, and these transport proteins are divided into importins and exportins (exporting molecules out of nucleus). The proteins imported in or exported out of nucleus include a nucleus-importing localization sequence (NLS) or nucleus-exporting localization sequence (NES) which can interact with the specific transport proteins. XPO1 (also referred to as CRM1 protein) is a most major nucleus exportin.

Cargo proteins of XPO1 include some specific tumor inhibitory proteins such as P53, P21, BRCA1, FOXOs, BCR-Abl, NPM and so on. A lot of research shows that XPO1 protein is highly expressed in various tumor types such as ovarian cancer, cervical cancer, osteosarcoma, lung cancer, pancreatic cancer, colon cancer, liver cancer, lymphoma and leukemia, and this high expression is related to poor prognosis effect of these tumors. The over-expression of XPO1 causes the tumor inhibitory proteins to be imported in cytoplasm and to be degraded such that the tumor inhibitory proteins lose tumor inhibitory action, which is considered a mechanism of cancer cells escaping from apoptosis. (Semin Cancer Biol. 2014, 27:74-86; Biochem Pharmacol. 2012, 83(8):1021-32.)

Tumor metastasis is a major reason for malignant tumors to be hardly treated and to have high mortality, and is also one of reasons for malignant tumors to show resistance to chemotherapy and radiotherapy. In addition, it is reported that most compounds having antitumor action is useless for tumor metastasis and for anti-radiotherapy and chemotherapy tumors (Methods Mol Med. 2005; 111:127-48). An active substance having antitumor metastasis action has very high clinical value, but such active substance is few disclosed in prior arts. Transition from epithelial cells to mesenchymal cells (Epithelial-Mesenchymal Transition, EMT) means an ability of epithelial cells morphologically transiting to fibrocytes or mesenchymal cell phenotypes and achieving migration, and plays a key role during metastasis of cancer cells. In recent years, EMT route has become a research focus for tumor metastasis. E-cadherin is an important cell adhesion molecule, and is closely related to genesis, invasion and metastasis of tumor. Snail protein is a transcription factor, can directly inhibit transcription of E-cadherin, and has an action of promoting cell migration. A lot of evidence has showed that expression level of Snail protein is up-regulated but expression level of E-cadherin is down-regulated before malignant tumor cells become metastatic, which improves tumor cell metastasis potency. Thus, a compound capable of inhibiting expression of Snail protein would have antitumor cell metastasis potential.

In addition to the tumor inhibitory proteins, the cargo proteins of XPO1 also include many key proteins related to inflammation and immune processes, such as IκB, Cox-2, RXRα, Commd1, HIF1 and so on. IκB is an NF-κB protein inhibitor, and binds to NF-κB in nucleus to inactive transcription function of NF-κB, thereby adjusting signal path of NF-κB which is closely related to inflammation and immune processes. In inflammation or immune misadjustment process, over-expression of XPO1 causes IκB to be degraded in cytoplasm such that IκB loses the regulating effect on NF-κB. (Shock. 2008, 29(2):160-6; J Biol Chem. 1999, 274(13):9108-15].

XPO1 protein is also responsible for nuclear export of retinoid receptor (RXRα). RXRα is highly expressed in liver, and plays a central role in metabolic regulation of bile acid, cholesterol, fatty acid, and steroid. In pathological process of liver inflammation, XPO1 protein is highly expressed which remarkably reduces retinol receptor level in nucleus. Thus, in the related pathological process such as inflammation or immune misadjustment, inhibiting over-expression of XPO1 protein is potentially beneficial. (J Biol Chem. 2006, 281(22):15434-40).

Inflammatory bowel disease (IBD) shows high morbidity worldwide, and number of people infected with inflammatory bowel disease per year in United States reaches up to two millions. In China, people infected with inflammatory bowel disease are rising year by year, inflammatory bowel disease has become a major reason for digestive system common diseases and chronic diarrhea, and patients are mostly children and young adults. Inflammatory bowel disease refers to various intestinal inflammatory diseases, mainly including ulcerative colitis and Crohn's disease. Pathogenesis of inflammatory bowel disease is still unclear, and is generally considered an immune system disease. Studies show that inflammation response is out of control in pathological process of inflammatory bowel disease, and some cytokines such as tumor necrosis factor TNF-α and interleukin molecule IL-6 are over-expressed and damage normal tissues and organs. Thus, treating inflammatory bowel disease generally needs to regulate over-expression of the cytokines (J Clin Invest. 2007; 117(3):514-21). Clinically, aminosalicylic acid formulation such as 5-aminosalicylic acid (5-ASA) and sulfasalazine can be used to treat inflammatory bowel disease, but such drug has certain curative effect only for mild cases, and generally has no curative effect and easily develops drug-resistance as well for severe cases. In addition, clinically, immunosuppressants such as cyclophosphamide and methotrexate can be used to suppress the immune response to own body. Unfortunately, these clinical therapeutic methods generally have very limited relieving effect on inflammatory bowel disease, and may have obvious toxic and side-effects including liver toxicity and bone marrow suppression toxicity. Searching a more safe and effective drug for inflammatory bowel disease has very great significance.

In addition to the above pathological processes, XPO1-mediated nuclear export is also closely related to package, integrity and maturity processes of various virion such as human immunodeficiency virus (HIV), influenza virus (H1N1 line, and fowl and bird H5N1 line), hepatitis B virus (HBV), hepatitis C virus (HCV), human papilloma virus (HPV), respiratory syncytial virus (RSV), dengue fever virus (Dungee), severe acute respiratory syndrome coronavirus, West Nile virus, herpes simplex virus (HSV), cyto- megalovirus (CMV), and Merkel cell polyomavirus (MCV). (Proc Natl Acad Sci USA. 2002, 99(22):14440-5; J Virol. 2008, 82(21):10946-52; J Biol Chem. 2009, 284(23):15589-97; J Virol. 2009; 83(11):5353-62). Thus, inhibiting the expression of XPO1 protein is also potentially beneficial for cutting off viral transport.

Semen raphani which has an alias of radish seed and a Latin name of Semen Raphani, is a traditional Chinese herbal medicine, and is mature seed of cruciferous plant radish. Semen raphani is generally used to relieve symptoms such as food retention and Qi stagnation, abdominal fullness and distention, belching, diarrhea, coughing and excessive phlegm, and dyspnea and chest congestion. Modern pharmacognostical studies show that its main active component is sulforaphene ($C_6H_9NOS_2$) which is an isothiocyanate compound. In previous studies, we were surprised to find that sulforaphene and its derivative are good XPO1 protein inhibitors, and have very good potential clinic application value.

SUMMARY OF THE INVENTION

We further find that sulforaphene derivative having a specific structure shows very excellent inhibitory activity for XPO1 protein, which is not disclosed in prior arts and previous studies of the inventor of the present invention.

One of objectives of the present invention is to provide a novel isothiocyanate compound which is an aryl substituted isothiocyanate compound having a structure of the general formula I:

wherein R is selected from phenyl, a five- to six-membered mononuclear heteroaryl including 1-3 heteroatoms each independently selected from nitrogen, oxygen or sulfur, an eight- to ten-membered dinuclear aryl, an eight- to ten-membered dinuclear heteroaryl including 1-4 heteroatoms each independently selected from nitrogen, oxygen or sulfur, a ten- to fourteen-membered trinuclear aryl, or a ten- to fourteen-membered trinuclear heteroaryl including 1-4 heteroatoms each independently selected from nitrogen, oxygen or sulfur;

R is unsubstituted, or is optionally substituted with one or more independently selected W substituents, the W substituent is selected from halogen, —$NO_2$, $C_{1-4}$ alkoxy, —CN, $C_{1-4}$ haloalkyl, —$SO_2NH_2$, $C_{1-4}$ alkyl, —$C_6H_5$, —$OC_6H_5$, —$OC_6H_4OCH_3$, —$SC_6H_5$, —$SC_6H_4OCH_3$, a five- to six-membered mononuclear heteroaryl including 1-3 heteroatoms each independently selected from nitrogen, oxygen or sulfur, a four- to seven-membered heterocycloalkyl including 1-3 heteroatoms each independently selected from nitrogen, oxygen or sulfur, or an eight- to ten-membered dinuclear heteroaryl including 1-4 heteroatoms each independently selected from nitrogen, oxygen or sulfur; and n is 0, 1 or 2.

Another object of the present invention is to provide a process for preparing the isothiocyanate compound, which comprises the following steps.

1. When n=1, the process for preparing the compound comprises the following steps:

(1) reacting a compound of the formula i with methylmethanesulfonic acid phosphoric acid diethyl ester for 12 h in the presence of potassium carbonate, using N,N-dimethylformamide (DMF) as a reaction solvent, to prepare a compound of the formula ii;

(2) reacting the compound of the formula ii with m-chloroperoxybenzoic acid (m-CPBA) in chloroform solution to produce a compound of the formula iii;

(3) reacting the compound of the formula iii with butyl-4-amino formic acid butyl ester aldehyde in the presence of lithium chloride in triethylamine/tetrahydrofuran (TEA/THF) solution to prepare a compound of the formula iv; and

(4) reacting the compound of the formula iv with trifluoroacetic acid in dichloromethane (DCM), followed by reacting with thiophosgene (CS2) in the presence of TEA in DCM to produce the compound of the formula I.

2. When n=2, the process for preparing the compound comprises the following steps:

(1) reacting a compound of the formula i with methylmethanesulfonic acid phosphoric acid diethyl ester for 12 h in the presence of potassium carbonate, using N,N-dimethylformamide (DMF) as a reaction solvent, to prepare a compound of the formula ii;

(2) reacting the compound of the formula ii with two equivalents of m-chloroperoxybenzoic acid (m-CPBA) in chloroform solution to produce a compound of the formula v;

(3) reacting the compound of the formula v with butyl-4-amino formic acid butyl ester aldehyde in the presence of lithium chloride in triethylamine/tetrahydrofuran (TEA/THF) solution to prepare a compound of the formula vi; and

(4) reacting the compound of the formula vi with trifluoroacetic acid in dichloromethane (DCM), followed by reacting with thiophosgene (CS2) in the presence of TEA in DCM to produce the compound of the formula I.

3. When n=0, the process for preparing the compound comprises the following steps:

(1) reacting a compound of the formula i with methylmethanesulfonic acid phosphoric acid diethyl ester for 12 h in the presence of potassium carbonate, using N,N-dimethylformamide (DMF) as a reaction solvent, to prepare a compound of the formula ii;

(2) reacting the compound of the formula ii with butyl-4-amino formic acid butyl ester aldehyde in the presence of lithium chloride in triethylamine/tetrahydrofuran (TEA/THF) solution to prepare a compound of the formula vii; and (3) reacting the compound of the formula vii with trifluoroacetic acid in dichloromethane (DCM), followed by reacting with thiophosgene (CS2) in the presence of TEA in DCM to produce the compound of the formula I.

Another objective of the present invention is to provide a XPO1 protein inhibitor drug that includes an effective dose of the isothiocyanate compound of the present invention.

The isothiocyanate compound of the present invention has very good solubility in water, far better inhibitory activity for XPO1 protein than other non-aryl substituted congeneric compounds, little side effect, and good biological safety and bioavailability, and is quite suitable for clinical application. Therefore, the isothiocyanate compound would have tremendous potential market space and economic benefits.

BRIEF DESCRIPTION OF THE DRAWINGS

Two figures are shown in the present specification.

DESCRIPTION OF THE PREFERRED EMBODIMENT

Unless specified otherwise, the terms used in the present invention have the following common meanings.

The term "halogen" represents a halogen substituent, and means fluoro-(—F), chloro-(—Cl), bromo-(—Br) or iodo-(—I); and the term "halogenated" means substituted with the above halogen substituent.

The term "alkyl" means a linear alkyl, branched alkyl or cycloalkyl. When "$C_{1-4}$ alkyl" is synoptically mentioned, it includes an alkyl with a free bond at one end, examples of which including but being not limited to methyl, ethyl, propyl, isopropyl, butyl, pri-/sec-/tert-butyl, cyclopropyl, methylcyclopropyl and cyclobutyl; and also includes an alkyl with two or more free bonds satisfying bond-valence theory, examples of which including but being not limited to —$CH_2$—, —$(CH_2)_2$—, —$(CH_2)_3$—, —$(CH_2)_4$— and —$C(CH_3)(CH_2)_2$—.

The term "phenyl" means an aryl having a benzene ring, and includes a substituted or unsubstituted —$C_6H_5$; and when "—$C_6H_5$" is mentioned, it merely means an unsubstituted phenyl.

The term "aryl" means a functional group or substituent derived from a simple aromatic ring; and unless specified otherwise, it may be a carboncylic aryl or a heterocylic aryl, may be a mononuclear aryl or a fused cyclic aryl, or may be a polynuclear substituent fused from an aryl ring and a non-aryl ring.

The term "heteroaryl" means a functional group or substituent derived from an aromatic ring including a heteroatom.

The term "haloalkyl" means an alkyl substituted with a halogen substituent.

The isothiocyanate compound of the present invention is an aryl-substituted isothiocyanate compound that has a structure of the general formula I:

wherein R is selected from phenyl, a five- to six-membered mononuclear heteroaryl including 1-3 heteroatoms each independently selected from nitrogen, oxygen or sulfur, an eight- to ten-membered dinuclear aryl, an eight- to ten-membered dinuclear heteroaryl including 1-4 heteroatoms each independently selected from nitrogen, oxygen or sulfur, a ten- to fourteen-membered trinuclear aryl, or a ten- to fourteen-membered trinuclear heteroaryl including 1-4 heteroatoms each independently selected from nitrogen, oxygen or sulfur.

R is preferably phenyl, furyl, thienyl, pyranyl, pyronyl, pyrryl, tetrazolyl, pyrazolyl, thiazolyl, imidazolyl, oxazolyl, pyridyl, pyridazinyl, pyrimidyl, pyrazinyl, or a di- to trinuclear group optionally fused from the above mononuclear groups, and in particular, R is preferably phenyl or a polynuclear aryl having phenyl. The above-mentioned "group optionally fused" includes a polynuclear aryl fused from different groups, such as benzofuryl, benzothienyl, indolyl (benzopyrryl), dibenzofuryl, dibenzothienyl, carbazolyl (dibenzopyrryl), benzothiazolyl, benzopyrazolyl, benzoimidazolyl, benzooxazolyl, quinolyl (benzopyridyl), isoquinolyl or the like, which are fused from phenyl and other group; and also includes a polynuclear aryl fused from same groups, such as naphthyl, anthryl, phenanthryl, pyrenyl or fluorenyl (dibenzocyclopentadiene).

Further, R is preferably phenyl, anthryl, phenanthryl, furyl, thienyl, pyrryl, tetrazolyl, benzofuryl, benzopyranyl, benzopyronyl, benzothienyl, indolyl, dibenzofuryl, dibenzothienyl, carbazolyl, pyrazolyl, thiazolyl, imidazolyl, oxazolyl, benzothiazolyl, benzopyrazolyl, benzoimidazolyl, benzooxazolyl, pyridyl, quinolyl, isoquinolyl, pyridazinyl, pyrimidyl, pyrazinyl, cinnolinyl, quinazolinyl, quinoxalinyl, phenoxazinyl, phenothiazinyl, phenazinyl or purinyl.

In the general formula I, R is unsubstituted, or is optionally substituted with one or more independently selected W substituent. Herein, "optionally substituted" means substituted with an optional substituent in an operable number at an optional position of the R group.

The W substituent is selected from halogen, —NO$_2$, C$_{1-4}$ alkoxy, —CN, C$_{1-4}$ haloalkyl, —SO$_2$NH$_2$, C$_{1-4}$ alkyl, —C$_6$H$_5$, —OC$_6$H$_5$, —OC$_6$H$_4$OCH$_3$, —SC$_6$H$_5$, —SC$_6$H$_4$OCH$_3$, a five- to six-membered mononuclear heteroaryl including 1-3 heteroatoms each independently selected from nitrogen, oxygen or sulfur, a four- to seven-membered heterocycloalkyl including 1-3 heteroatoms each independently selected from nitrogen, oxygen or sulfur, or an eight- to ten-membered dinuclear heteroaryl including 1-4 heteroatoms each independently selected from nitrogen, oxygen or sulfur.

In a preferable embodiment, the W substituent is selected from halogen, C$_{1-4}$ alkoxy, —CN, C$_{1-4}$ haloalkyl, —SO$_2$NH$_2$, —C$_6$H$_5$, —OC$_6$H$_5$, —OC$_6$H$_4$OCH$_3$, —SC$_6$H$_5$, —SC$_6$H$_4$OCH$_3$, a five- to six-membered mononuclear heteroaryl including 1-3 heteroatoms each independently selected from nitrogen, oxygen or sulfur, or a four- to seven-membered heterocycloalkyl including 1-3 heteroatoms each independently selected from nitrogen, oxygen or sulfur. More preferably, the W substituent is selected from Cl, Br, —OCH$_3$, —CF$_3$, —SO$_2$NH$_2$, —CN, —C$_6$H$_5$, —OC$_6$H$_5$, —OC$_6$H$_4$OCH$_3$, —SC$_6$H$_5$, —SC$_6$H$_4$OCH$_3$, or morpholinyl.

In the general formula I, n is selected from 0, 1 or 2, preferably n=1 or 2, most preferably n=1.

Various specific embodiments for the isothiocyanate compound of the present invention can be optionally combined so as to obtain preferable embodiments for the isothiocyanate compound of the present invention.

In a specific embodiment, the isothiocyanate compound of the present invention is selected from the following compounds:

I-01

I-02

I-03

I-04

I-05

I-06

I-07

I-08

I-09

US 10,315,990 B2

9 -continued | 10 -continued

-continued

I-27

I-28

The isothiocyanate compound of the present invention also includes all isomers represented by the general formula I, and includes, but is not limited to, enantiomer and diastereoisomer of each structural formula; R and S configurational compounds of each asymmetric center, Z and E double-bond isomers, and Z and E conformational isomers.

In addition, the isothiocyanate compound of the present invention further includes a pharmaceutically acceptable salt formed from the compound of the general formula I, and examples thereof include a pharmaceutically acceptable salt without toxicity to human body. The non-toxic salt preferably includes an alkali metal salt or alkaline-earth metal salt such sodium salt, potassium salt and calcium salt; a hydrohaloride such as hydrofluoride, hydrochloride, hydrobromide and hydriodate; an inorganic acid salt such as nitrate, perchlorate, sulfate and phosphate; an organic acid salt such as mesylate, fumarate, succinate, citrate, tartrate, oxalate and maleate; and an amino acid salt such as glutamate and aspartate.

Another subject of the present invention is to provide an XPO1 protein inhibitor drug including an effective dose of the isothiocyanate compound of the present invention.

In a specific embodiment, the XPO1 protein inhibitor drug is an XPO1 protein inhibitor anti-inflammatory drug, an XPO1 protein inhibitor antitumor drug, or an XPO1 protein inhibitor antiviral drug.

In a more specific embodiment, the XPO1 protein inhibitor anti-inflammatory drug is a drug for treating an inflammatory bowel disease, or the XPO1 protein inhibitor antitumor drug is an antitumor metastasis drug.

The tumor treated with the antitumor metastasis drug is selected from lung cancer, breast cancer, ovarian cancer, colon cancer, pancreatic cancer, esophagus cancer, osteosarcoma, kidney cancer, cervical cancer, bladder cancer, head and neck cancers, multiple myeloma, brain cancer, prostatic cancer, melanoma, gastric cancer, liver cancer, neuroglioma, oral cancer, nasopharyngeal cancer, laryngeal cancer, hypophysoma, soft tissue sarcoma, thyroid cancer, testicular cancer, gallbladder cancer, salivary gland cancer, urethral cancer, uterine sarcomas, leukemia, and lymphoma.

The XPO1 protein inhibitor drug of the present invention can be formed into any dosage form in accordance with its application, and examples of the dosage form includes, but are not limited to, oral dosage forms such as tables, capsules, granules, powders, pills, fine granules, lozenges, syrups and emulsions; injections such as intravenous injections and intramuscular injections; and dosage forms via rectal administration such as greasy suppositories, water-soluble suppositories and ointments. These dosage forms can be prepared by an ordinary method using pharmaceutically acceptable carriers such as excipient, filler, adhesive, wetter, disintegrant, surfactant, lubricant, dispersant, buffer, pH regulator, conservant, chelating agent, cosolvent, preservative, flavoring agent, soothing agent, and stabilizer.

The XPO1 protein inhibitor antitumor drug of the present invention may be applied solely or in combination with other antitumor therapy means. The combined application is selected from an application in combination with a surgical operation, an application in combination with one or more western medicines, an application in combination with a Chinese herbal medicine, an application in combination with a radioactive therapy, an application in combination with a gene therapy, or an application in combination with a biology regulator.

The following examples are shown in the present invention to make the present invention to be easily understood. The person skilled in the art should understand that these examples merely help to make the present invention to be understood, other than specifically limiting the present invention.

Example 1. Preparation of Compound I-01

Step 1. Preparation of (2-ethyl)-thiophenol-methylphosphoric Acid Ethyl Ester

1.10 g of thiophenol and 1.88 g of potassium carbonate were dissolved in 45 ml of DMF solution, 1.65 g of (diethoxyphosphoryl)methyl 4-methylbenzenesulfonate was slowly dripped therein at room temperature and stirred at room temperature, TLC detection was performed and it was confirmed that raw materials no longer decreased after 2 hours, and the reaction was completed. Organic layer was extracted, combined and dried, and column chromatography was carried out to obtain 2.20 g of a yellow oily liquid (yield 88%). Mass spectrum MS of the compound: $[M+H]^+$ 260.0.

Step 2. Preparation of (2-ethyl)-1-benzenesulfinyl-methylphosphoric Acid Ethyl Ester

2.66 g of the product obtained in the step 1 was dissolved in 25 ml of chloroform solution, 0.25 g of m-CPBA solution was slowly dripped therein and stirred at room temperature, TLC detection was performed and it was confirmed that raw materials no longer decreased after 1 hour, and the reaction was completed. Organic layer was extracted, combined and dried, and column chromatography was carried out to obtain 2.21 g of an oily liquid (yield 85%). Mass spectrum MS of the compound: [M+H]+276.3.

Step 3

2.70 g of the product obtained in the step 2 and 0.17 g of lithium chloride powder were dissolved in 25 ml of TEA/THF solution, 1.17 g of butyl-4-amino formic acid butyl ester aldehyde was slowly added in the solution and stirred at room temperature, TLC detection was performed and it was confirmed that raw materials no longer decreased after half an hour, and the reaction was completed. Organic layer was extracted, combined and dried, separation was carried out by preparation liquid chromatography MPLC (eluent: PE:EtOAc=1:1) to obtain an oily liquid. The oily liquid was then dissolved in 10 ml of trifluoroacetic acid solution, 5 ml of DCM was added therein, and reacted at room temperature for 1 hour. Organic layer was extracted, combined and dried, and column chromatography was carried out to obtain 2.10 g of a white solid. 25 ml of DCM solution in which thiophosgene ($CS_2$) was dissolved was slowly dripped in the solid and stirred at room temperature, TLC detection was performed and it was confirmed that raw materials no longer decreased after half an hour, TEA aqueous solution was added to terminate the reaction. Organic layer was extracted, combined and dried, and column chromatography was carried out to obtain 1.55 g of a brown yellow oily liquid (yield 76%) which is the compound I-01. Mass spectrum MS: [M+H]+203.3. Nuclear magnetic resonance hydrogen spectrum ($^1$H-NMR: DMSO): δ 7.66 (2H, d), δ 7.52 (2H, m), δ 7.27 (1H, m), δ 6.56 (1H, m), δ 6.42 (1H, d), δ 3.67 (2H, m), δ 2.64 (2H, m).

Example 2. Preparation of Compound I-04

Step 1. Preparation of diethyl [(4-methylbenzenesulfonyl)oxy]methanephosphonate 2.46 g of 3,5-bistrifluoromethylthiophenol and 1.40 g of potassium carbonate were dissolved in 35 ml of DMF solution, 1.50 g of (diethoxyphosphoryl)methyl 4-methylbenzenesulfonate was slowly dripped therein at room temperature and stirred at room temperature, TLC detection was performed and it was confirmed that raw materials no longer decreased after 2 hours, and the reaction was completed. Organic layer was extracted, combined and dried, and column chromatography was carried out to obtain 3.13 g of a yellow oily liquid (yield 89%). Mass spectrum MS of the compound: [M+H]$^+$397.1.

Step 2. Preparation of diethyl (((3,5-bis(trifluoromethyl)phenyl)sulfinyl)methyl)phosphonate 4.00 g of the product obtained in the step 1 was dissolved in 50 ml of chloroform solution, 0.35 g of m-CPBA solution was then slowly dripped therein and stirred at room temperature, TLC detection was performed and it was confirmed that raw materials no longer decreased after 1 hour, and the reaction was completed. Organic layer was extracted, combined and dried, and column chromatography was carried out to obtain 3.61 g of an oily liquid (yield 90%). Mass spectrum MS of the compound: [M+H]+412.3.

Step 3

4.20 g of the product obtained in the step 2 and 0.11 g of lithium chloride powder were dissolved in 35 ml of TEA/THF solution, 1.17 g of butyl-4-amino formic acid butyl ester aldehyde was slowly added in the solution and stirred at room temperature, TLC detection was performed and it was confirmed that raw materials no longer decreased after half an hour, and the reaction was completed. Organic layer was extracted, combined and dried, separation was carried out by preparation liquid chromatography MPLC (eluent: PE:EtOAc=1:1) to obtain an oily liquid. The oily liquid was then dissolved in 15 ml of trifluoroacetic acid solution, 5 ml of DCM was added therein, and reacted at room temperature for 1 hour. Organic layer was extracted, combined and dried, and column chromatography was carried out to obtain 3.82 g of a white solid. 25 ml of DCM solution in which thiophosgene ($CS_2$) was dissolved was slowly dripped in the solid and stirred at room temperature, TLC detection was performed and it was confirmed that raw materials no longer decreased after half an hour, TEA aqueous solution was added to terminate the reaction. Organic layer was extracted, combined and dried, and column chromatography was carried out to obtain 3.10 g of a yellow oily liquid (yield 82%) which is the compound I-04.

Mass spectrum MS of the compound I-04: [M+H]+373.3. Nuclear magnetic resonance hydrogen spectrum of the compound I-04 ($^1$H-NMR: DMSO): δ 7.84 (2H, d), δ 7.60 (1H, s), δ 7.52 (2H, m), δ 6.57 (1H, m), δ 6.40 (1H, d), δ 3.64 (2H, m), δ 2.61 (2H, m).

Example 3. Preparation of Compound I-21

Step 1. Preparation of 5-trifluoromethyl-benzothiazolethiol

2.40 g of 2-bromo-5-trifluoromethyl-aniline and 1.21 g of potassium ethylxanthate were dissolved in 35 ml of DMF solution, reacted under refluxing at 120 degree centigrade, and then reacted overnight under stirring at room temperature. TLC detection was performed and it was confirmed that raw materials no longer decreased, and the reaction was completed. The product was washed with 25 ml of dilute hydrochloric acid solution, organic layer was extracted, combined and dried, and column chromatography was carried out to obtain 1.70 g of an oily liquid (yield 72%). Mass spectrum MS of the compound: [M+H]$^+$235.2.

Step 2. Preparation of diethyl (((5-(trifluoromethyl) benzo[d]thiazol-2-yl)thio)methyl)phosphonate

2.35 g of the product obtained in the step 1 and 1.38 g of potassium carbonate were dissolved in 50 ml of DMF solution, 1.50 g of (diethoxyphosphoryl)methyl 4-methylbenzenesulfonate was slowly dripped therein at room temperature and stirred at room temperature, TLC detection was performed and it was confirmed that raw materials no longer decreased after 4 hours, and the reaction was completed. Organic layer was extracted, combined and dried, and column chromatography was carried out to obtain 2.27 g of a yellow oily liquid (yield 88%). Mass spectrum MS of the compound: [M+H]$^+$281.1.

Step 3. Preparation of diethyl ({[5-(trifluoromethyl)-1,3-benzothiazol-2-yl]sulfinyl}methyl)phosphonate

2.80 g of the product obtained in the step 2 and 1.38 g of potassium carbonate were dissolved in 35 ml of DMF solution, 1.50 g of phenylmethanesulfonic acid phosphoric acid diethyl ester was slowly dripped therein at room temperature and stirred at room temperature, TLC detection was performed and it was confirmed that raw materials no longer decreased after 3 hours, and the reaction was completed. Organic layer was extracted, combined and dried, and column chromatography was carried out to obtain 3.10 g of a yellow oily liquid with a yield of 81%. Mass spectrum MS of the compound: [M+H]$^+$385.2.

Step 4

3.90 g of the product obtained in the step 3 and 0.11 g of lithium chloride powder were dissolved in 25 ml of TEA/THF solution, 1.17 g of butyl-4-amino formic acid butyl ester aldehyde was slowly added in the solution and stirred at room temperature, TLC detection was performed and it was confirmed that raw materials no longer decreased after half an hour, and the reaction was completed. Organic layer was extracted, combined and dried, separation was carried out by preparation liquid chromatography MPLC (eluent: PE:EtOAc=1:1) to obtain an oily liquid. The oily liquid was then dissolved in 15 ml of trifluoroacetic acid solution, 3 ml of DCM was added therein, and reacted at room temperature for 1 hour. Organic layer was extracted, combined and dried, and column chromatography was carried out to obtain 2.92 g of a white solid. 25 ml of DCM solution in which thiophosgene (CS$_2$) was dissolved was slowly dripped in the solid and stirred at room temperature, TLC detection was performed and it was confirmed that raw materials no longer decreased after half an hour, TEA aqueous solution was added to terminate the reaction. Organic layer was extracted, combined and dried, and column chromatography was carried out to obtain 2.71 g of a brown yellow oily liquid (yield 80%) which is the representative compound I-21. Mass spectrum MS: [M+H]+362.0. Nuclear magnetic resonance hydrogen spectrum ($^1$H-NMR: DMSO): δ 8.42 (1H, d), δ 8.05 (1H, d), δ 7.74 (1H, m), δ 6.75 (1H, m), δ 6.38 (1H, d), δ 3.63 (2H, m), δ 2.41 (2H, m).

Example 4. Preparation of Compound I-25

Step 1. Preparation of diethyl [(4-methylbenzenesulfonyl)oxy]methanephosphonate 0.76 g of 1-phenyl-1H-tetrazole-5-thiol and 1.38 g of potassium carbonate were dissolved in 50 ml of DMF solution, 1.50 g of diethyl [(4-methylbenzenesulfonyl)oxy] methanephosphonate was slowly dripped therein at room temperature and stirred at room temperature, TLC detection was performed and it was confirmed that raw materials no longer decreased after 2 hours, and the reaction was completed. Organic layer was extracted, combined and dried, and column chromatography was carried out to obtain 0.71 g of a yellow oily liquid (yield 72%). Mass spectrum MS of the compound: [M+H]$^+$226.1.

Step 2: Preparation of diethyl (((1-phenyl-1H-tetrazol-5-yl)sulfinyl)methyl)phosphonate

2.26 g of the product obtained in the step 1 was dissolved in 15 ml of chloroform solution, 0.25 g of m-CPBA solution was then slowly dripped therein and stirred at room temperature, TLC detection was performed and it was confirmed that raw materials no longer decreased after 1 hour, and the reaction was completed. Organic layer was extracted, combined and dried, and column chromatography was carried out to obtain 1.92 g of an oily liquid (yield 81%). Mass spectrum MS of the compound: [M+H]+242.3.

Step 3

2.42 g of the product obtained in the step 2 and 0.30 g of lithium chloride powder were dissolved in 25 ml of TEA/THF solution, 1.21 g of butyl-4-amino formic acid butyl ester aldehyde was slowly added in the solution and stirred at room temperature, TLC detection was performed and it was confirmed that raw materials no longer decreased after half an hour, and the reaction was completed. Organic layer was extracted, combined and dried, separation was carried out by preparation liquid chromatography MPLC (eluent: PE:EtOAc=1:1) to obtain an oily liquid. The oily liquid was then dissolved in 15 ml of trifluoroacetic acid solution, 5 ml of DCM was added therein, and reacted at room temperature for 1 hour. Organic layer was extracted, combined and dried, and column chromatography was carried out to obtain 2.61 g of a white solid. 25 ml of DCM solution in which thiophosgene (CS$_2$) was dissolved was slowly dripped in the solid and stirred at room temperature, TLC detection was performed and it was confirmed that raw materials no longer decreased after half an hour, TEA aqueous solution was added to terminate the reaction. Organic layer was extracted, combined and dried, and column chromatography was carried out to obtain 2.47 g of a yellow oily liquid (yield 81%) which is the representative compound I-25.

-continued

Mass spectrum MS of the compound I-25: [M+H]+305.3. Nuclear magnetic resonance hydrogen spectrum of the compound I-25 ($^1$H-NMR: DMSO): δ 7.36 (2H, m), δ 7.30 (1H, m), δ 7.25 (2H, m), δ 6.57 (1H, m), δ 6.40 (1H, d), δ 3.64 (2H, m), δ 2.51 (2H, m).

Example 5. Preparation of Compound I-27

Step 1: Preparation of 4-phenoxythiophenol

1.86 g of 4-phenoxyphenol, 1.23 g of dimethylamino-2-thiocarbonyl chloride and 0.24 g of sodium hydride were dissolved in 35 ml of DMF solution and reacted at room temperature. After washed with 25 ml of sodium hydroxide solution and methanol, organic layer was extracted to obtain 1.07 g of an oily liquid (yield 52%). Mass spectrum MS of the compound: [M+H]+202.2.

Step 2

2.30 g of the product obtained in the step 1 and 1.38 g of potassium carbonate were dissolved in 35 ml of DMF solution, 1.50 g of methylmethanesulfonic acid phosphoric acid diethyl ester was then slowly dripped therein at room temperature and stirred at room temperature, TLC detection was performed and it was confirmed that raw materials no longer decreased after 2 hours, and the reaction was completed. Organic layer was extracted, combined and dried, and column chromatography was carried out to obtain 2.50 g of a yellow oily liquid (yield 72%). Mass spectrum MS of the compound: [M+H]$^+$352.3.

Step 3

3.50 g of the product obtained in the step 2 was dissolved in 35 ml of chloroform solution, 0.25 g of m-CPBA solution was then slowly dripped therein and stirred at room temperature, TLC detection was performed and it was confirmed that raw materials no longer decreased after 2 hours, and the reaction was completed. Organic layer was extracted, combined and dried, and column chromatography was carried out to obtain 2.94 g of an oily liquid (yield 80%). Mass spectrum MS of the compound: [M+H]+368.3.

Step 4

3.60 g of the product obtained in the step 3 and 0.25 g of lithium chloride powder were dissolved in 35 ml of TEA/ THF solution, 1.21 g of butyl-4-amino formic acid butyl ester aldehyde was slowly added in the solution and stirred at room temperature, TLC detection was performed and it was confirmed that raw materials no longer decreased after half an hour, and the reaction was completed. Organic layer was extracted, combined and dried, separation was carried out by preparation liquid chromatography MPLC (eluent: PE:EtOAc=1:1) to obtain an oily liquid. The oily liquid was then dissolved in 15 ml of trifluoroacetic acid solution, 5 ml of DCM was added therein, and reacted at room temperature for 1 hour. Organic layer was extracted, combined and dried, and column chromatography was carried out to obtain 2.95 g of a white solid. 25 ml of DCM solution in which thiophosgene (CS$_2$) was dissolved was slowly dripped in the solid and stirred at room temperature, TLC detection was performed and it was confirmed that raw materials no longer decreased after half an hour, TEA aqueous solution was added to terminate the reaction. Organic layer was extracted, combined and dried, and column chromatography was carried out to obtain 2.07 g of a yellow oily liquid (yield 63%) which is the compound I-27. Mass spectrum MS: [M+H]+ 329.1. Nuclear magnetic resonance hydrogen spectrum ($^1$H-NMR: DMSO): δ 7.61 (2H, m), δ 7.22 (2H, m), δ 7.14 (2H, m), δ 6.98 (1H, m), δ 6.92 (2H, m), δ 6.57 (1H, m), δ 6.40 (1H, d), δ 3.64 (2H, m), δ 2.51 (2H, m).

Example 6. Measurement of Inhibitory Activity of Representative Compound for XPO1 Protein NES (nuclear export signal) is a nuclear export signal peptide recognized by XPO1 protein. XPO1 recognizes NES sequence peptide segment of biomacromolecule and exports the biomacromolecule out of nucleus. NES-GFP protein is obtained by co-expressing green fluorescence protein GFP and NES sequence peptide segment by using a eukaryotic expression plasmid. Inhibitory activity of the representative compound for XPO1 protein can be assessed by detecting influence of the compound on NES-GFP cell localization.

Figure 1:
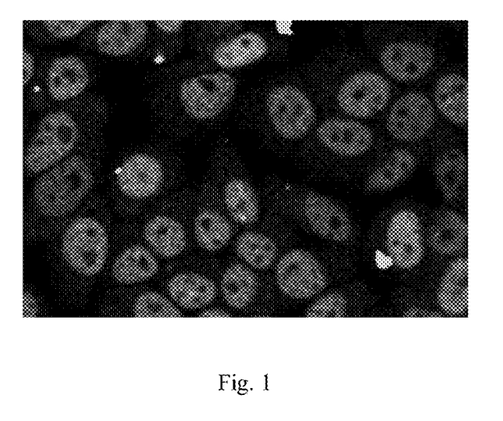
FIG. 1 is a laser confocal micrograph showing effect of the representative compound I-01 for target binding XPO1 protein and inhibiting nuclear export thereof.

The cells were digested with trypsin, counted, and inoculated on 96-well plate in an amount of 1.5×10$^4$ cells per well. Sixteen hours later, NES-GFP plasmid was transfected with liposome. Twenty-four hours later, each representative compound solution, SFN molecule solution and PEITC molecule solution were added to treat for 2 hours respectively, and then 100 μl of Hochest 33258 (1 mg/ml) was added to stain nucleus. Inhibitory effect on NES-GFP nuclear export was observed with a laser confocal microscope (Olympus-IX71) and expressed as percentage. Results are shown in FIG. 1 and Table 1.

In the present invention, SFE is sulforaphene, SFN is sulforaphane (C$_6$H$_{11}$NOS$_2$), and PEITC is phenylethylisothiocyanate (C$_9$H$_9$NS) which are used as control compounds in the experiment, and other compounds have the following structural formulae which can be obtained by the process of the present invention using corresponding material compounds respectively.

Sulforaphene (SFE)

F-01 = (E)-4-isothiocyanato-1-(propylsulfinyl)but-1-ene

F-03 = (E)-((4-isothiocyanatobut-1-en-1-yl)sulfinyl)cyclopropane

F-04 = (E)-1-(isobutylsulfinyl)-4-isothiocyanatobut-1-ene

F-05 = (E)-4-isothiocyanato-1-(methylsulfonyl)but-1-ene

F-06 = (E)-(4-isothiocyanatobut-1-en-1-yl)(methyl)sulfane

The laser confocal micrograph showing the inhibitory effect of the representative compound I-01 for XPO1 is specifically shown in FIG. 1. It can be seen from FIG. 1 that most of NES-GFP protein emitting green fluorescence is congregated in nucleus, which proves the representative compound has good inhibitory activity for XPO1 protein.

The experimental results show that each representative compound of the present invention has good inhibitory activity for XPO1 protein, and that the inhibitory activity of the compound of the present invention for XPO1 protein is several times to hundreds of times higher than that of two natural compounds SFN and PEITC, and is also remarkably better than that of non-aryl substituted congeneric compounds represented by sulforaphene. The specific results are shown in Table 1.

TABLE 1

Inhibitory activity of the compound of the present invention for XPO1 protein (full inhibitory concentration)

| Compound | Activity (μM) | Compound | Activity (μM) | Compound | Activity (μM) |
|---|---|---|---|---|---|
| SFN | 35 | PEITC | 30 | | |
| SFE | 10-15 | F-01 | 10-15 | F-03 | 5-10 |
| F-04 | 10-15 | F-05 | 10-15 | F-06 | 15-20 |
| I-01 | 1-5 | I-02 | 1-5 | I-03 | 0.5-1 |
| I-04 | 0.250 | I-05 | 0.5-1 | I-06 | 0.200 |
| I-07 | 0.5-1 | I-08 | 0.5-1 | I-09 | 1-5 |
| I-10 | 1-5 | I-11 | 1-5 | I-12 | 1-5 |
| I-13 | 1-5 | I-14 | 1-5 | I-15 | 1-5 |
| I-16 | 0.5-1 | I-17 | 0.5-1 | I-18 | 1-5 |
| I-19 | 1-5 | I-20 | 1-5 | I-21 | 1-5 |
| I-22 | 1-5 | I-23 | 1-5 | I-24 | 1-5 |
| I-25 | 1-5 | I-26 | 0.5-1 | I-27 | 0.5-1 |
| I-28 | 0.5-1 | | | | |

Example 7. Evaluation on Macroscopic Pathological Changes of IBD Animal Model Treated with Representative Compound Eight-week-old male SD rats (10 rats per group) were fasted for 24 hours and anaesthetized with diethyl ether. 50% ethanol and TNBS (2,4,6-trinitrobenzenesulfonic acid) were mixed to prepare a solution. In the IBD model group, a tube made of vinyl resin was inserted 5 cm from anus, and enteroclysis was performed with the TNBS solution in a dose of 100 mg/kg. The rats were hung upside down 30 seconds later after the enteroclysis to ensure no leakage of the TNBS solution. In the control group, the TNBS solution was replaced with normal saline with which enteroclysis was performed. Seven days later after the enteroclysis with the TNBS solution or normal saline, animals were sacrificed and dissected. In each of the drug-treated groups, each representative compound, SFE, SFN and PEITC were intragastrically administrated daily in a dose of 80 mg/kg from one day before the enteroclysis with TNBS. Two weeks later after treated with the drugs, the animals were sacrificed and dissected, and large intestine thereof was taken out and fixed in 4% formalin solution for 30 minutes. The large intestine of the animals was cut lengthwise from the mesentery side to take photos for rectum portion and measure the weight of rectum. Based on the macroscopic observation and judgment score (Table 2-1), ulceration and bleeding states of rectum portion were scored according to the macroscopic observation scoring standard.

TABLE 2-1

Macroscopic observation and judgment scoring standard

| Score (0-5) | Macroscopic observation standard |
|---|---|
| 0 | No inflammation, no erosion and no bleeding |
| 1 | Small scale erosion and slight swelling |
| 2 | Mild erosion, swelling and turning red |
| 3 | Moderate erosion and slight bleeding |
| 4 | Small scale severe erosion and bleeding |
| 5 | Large scale severe erosion and bleeding |

The specific macroscopic judgment scores after treated with the representative compound of the present invention are shown in Table 2-2. It can be seen from the results that compared to the normal saline enteroclysis group, the TNBS enteroclysis group shows relatively remarkable colon tissue ulceration, bleeding and necrosis phenomena, and has a relatively high macroscopic pathological judgment score. The 5-ASA-treated group, SFN-treated group and PEITC-treated group merely show a small relief extent in colon tissue bleeding and ulceration phenomena. Compared to these, the group treated with each representative compound shows little colon tissue damage and greatly relieved colon tissue bleeding and ulceration phenomena, proving that the test compound of the present invention provides good protection and therapeutic effect on IBD, which is remarkably better than the 5-ASA-treated group, SFN-treated group and PEITC-treated group, and is also remarkably better than the non-aryl substituted isothiocyanate compounds represented by sulforaphene.

TABLE 2-2

Macroscopic observation and judgment score of IBD animal model treated with part of representative compound

| Group | Dose | Animal number | Macroscopic pathological score |
|---|---|---|---|
| Normal saline | 100 mg/kg | 10 | 0 |
| Enteroclysis with TNBS | 100 mg/kg | 10 | 4.5 ± 0.3 |
| Treated with 5-ASA | 80 mg/kg | 10 | 4.0 ± 0.2 |
| Treated with SFN | 80 mg/kg | 10 | 4.0 ± 0.5 |
| Treated with PEITC | 80 mg/kg | 10 | 3.5 ± 0.3 |
| Treated with I-01 | 80 mg/kg | 10 | 2.5 ± 0.1 |
| Treated with I-02 | 80 mg/kg | 10 | 2.0 ± 0.4 |
| Treated with I-04 | 80 mg/kg | 10 | 1.0 ± 0.5 |
| Treated with I-06 | 80 mg/kg | 10 | 1.0 ± 0.1 |
| Treated with I-20 | 80 mg/kg | 10 | 2.0 ± 0.3 |
| Treated with I-25 | 80 mg/kg | 10 | 1.5 ± 0.3 |
| Treated with SFE | 80 mg/kg | 10 | 3.0 ± 0.5 |
| Treated with F-03 | 80 mg/kg | 10 | 2.5 ± 0.6 |
| Treated with F-05 | 80 mg/kg | 10 | 3.0 ± 0.1 |
| Treated with F-06 | 80 mg/kg | 10 | 3.5 ± 0.2 |

Example 8. Evaluation Test of Representative Compound in Inhibiting Cytokine Level Change Caused by NF-κB Signal Path Inflammatory bowel disease is an autoimmune disease. It is found in the experiment that the representative compound of the present invention regulates NF-κB which is a key signal path directly related to immune system disease and inflammation, by inhibiting XPO1 protein. The therapeutic effect of the representative compound for the immune system disease or inflammation can be assessed by detecting change in levels of some important cytokines such as TNF-α and IL-6 at downstream of the signal path. Three days later after making the TNBS model (disease high-incidence season) in the Example 7, serums of three animals from each of the control animal group, model animal group and drug-treated group were collected, protein and tRNA were extracted, and levels of cytokines TNF-α and IL-6 in the serums were detected by the ELISA method, respectively. The results show that the drug-treated group animals treated with the representative compound of the present invention show significantly decreased levels of cytokines TNF-α and IL-6 in the serum compared to the model group, showing that the representative compound has significant regulating effect on the NF-κB signal path and has very good therapeutic effect on inflammatory bowel disease. The change in levels of TNF-α and IL-6 of the IBD model treated with the representative compound is specifically shown in Table 3 and Table 4.

TABLE 3

Serum TNF-α level of IBD animal model treated with representative compound (ng/ml)

| Group | Dose | Animal-1 | Animal-2 | Animal-3 |
|---|---|---|---|---|
| Control | — | 0.6 | 0.3 | 0.4 |
| IBD model | — | 2.5 | 2.1 | 2.2 |
| 5-ASA | 80 mg/kg | 1.7 | 1.8 | 2.0 |
| SFN | 80 mg/kg | 2.1 | 1.8 | 2.1 |
| PEITC | 80 mg/kg | 2.0 | 1.9 | 2.0 |
| I-01 | 80 mg/kg | 1.5 | 1.2 | 1.2 |
| I-03 | 80 mg/kg | 1.3 | 1.1 | 0.7 |
| I-06 | 80 mg/kg | 0.9 | 0.6 | 0.5 |
| I-08 | 80 mg/kg | 1.0 | 1.2 | 1.1 |
| I-20 | 80 mg/kg | 1.3 | 1.2 | 1.1 |
| I-25 | 80 mg/kg | 1.0 | 0.5 | 0.8 |
| SFE | 80 mg/kg | 1.8 | 1.8 | 1.7 |
| F-01 | 80 mg/kg | 2.0 | 1.7 | 1.9 |
| F-03 | 80 mg/kg | 1.7 | 1.6 | 1.5 |
| F-06 | 80 mg/kg | 2.3 | 2.0 | 2.2 |

TABLE 4

Serum IL-6 level of IBD animal model treated with representative compound (ng/ml)

| Group | Dose | Animal-1 | Animal-2 | Animal-3 |
|---|---|---|---|---|
| Control | — | 0.4 | 0.3 | 0.1 |
| IBD model | — | 3.0 | 2.5 | 2.6 |
| 5-ASA | 80 mg/kg | 2.7 | 2.2 | 2.3 |
| SFN | 80 mg/kg | 2.5 | 2.4 | 2.3 |
| PEITC | 80 mg/kg | 2.2 | 2.1 | 2.1 |
| I-01 | 80 mg/kg | 1.5 | 1.3 | 1.2 |
| I-03 | 80 mg/kg | 0.9 | 0.8 | 0.7 |
| I-06 | 80 mg/kg | 0.7 | 0.5 | 0.3 |
| I-08 | 80 mg/kg | 0.8 | 0.7 | 0.8 |
| I-20 | 80 mg/kg | 1.0 | 1.1 | 1.0 |
| I-25 | 80 mg/kg | 0.6 | 0.7 | 0.5 |
| SFE | 80 mg/kg | 2.0 | 1.9 | 1.9 |

TABLE 4-continued

Serum IL-6 level of IBD animal model treated with representative compound (ng/ml)

| Group | Dose | Animal-1 | Animal-2 | Animal-3 |
|---|---|---|---|---|
| F-01 | 80 mg/kg | 1.8 | 1.9 | 2.0 |
| F-03 | 80 mg/kg | 1.7 | 1.8 | 1.8 |
| F-06 | 80 mg/kg | 2.8 | 2.5 | 2.3 |

Example 9. Safety Testing of Representative Compound Via Oral Administration

The compound solution was intragastrically administrated to 6-week-old male and female SD rats (I-01: 500 mg/kg/day; I-03: 500 mg/kg/day; I-04: 500 mg/kg/day, I-06: 500 mg/kg/day, I-11: 300 mg/kg/day) for 6 weeks continuously (n=10 per group). The results are that no abnormity in general status, weight change, food consumption or tissue pathology was observed in the animals of any dose group. It can be seen from these results that the nontoxic dose of the compounds I-01, I-03, I-04, I-06 is at least 500 mg/kg/day, and the nontoxic dose of the compound I-11 is at least 300 mg/kg/day. The experimental results show that these representative compounds are compounds with little toxicity.

Example 10. Detection of Inhibitory Activity of Representative Compound for Formation of HMLE-Snail Cell Line Spheroids HMLE-Snail cell line is one of most classic cell models for studying tumor cell metastasis and EMT path. HMLE-Snail cell line highly expresses Snail protein, and thus one of most remarkable features thereof is that it has spherical cellular morphology (spheroid). Thus, the ability of the representative compound in inhibiting EMT path and consequently inhibiting tumor cell metastasis can be assessed by detecting the inhibitory activity of the representative compound for the formation of HMLE-Snail cell line spheroids (Cell 2008, 133:704-715). The HMLE-Snail cell line used in the present invention was donated by Dr. Robert Weinberg from America Massachusetts Whitehead Institute. HMLE-Snail cells were suspended in a liquid culture medium (in which B-27 and N-2 were added, purchased from America Invitrogen Corporation) containing DMEM/F12 in a ratio of 1:1, in an amount of $1.0 \times 10^3$ cells/ml, and cultured in an ultra low attachment culture plate so as to allow spheroids to be formed. Seven days later, spheroids were collected by centrifugation, and counted. The formation of cell spheroids was observed with microscope, and inhibitory activities of 10 μg/ml of SFN molecule, 10 μg/ml of PEITC molecule, 10 μg/ml of docetaxel, and 10 μg/ml of each representative compound, with which HMLE-Snail cells were treated for 24 hours, for the formation of HMLE-Snail cell line spheroids, were evaluated respectively. Detection effects are shown in Table 5. Docetaxel is a common clinical chemotherapy drug.

TABLE 5

Inhibitory activity of representative compound for formation of HMLE-Snail cell line colony

| Compound | Colony (%) | Compound | Colony (%) | Compound | Colony (%) |
|---|---|---|---|---|---|
| Control | 100 | SFN | 90 | PEITC | 85 |
| Docetaxel | 81 | I-01 | 35-40 | I-02 | 30-35 |
| I-03 | 25-30 | I-04 | 10-15 | I-05 | 20-25 |
| I-06 | 10-15 | I-07 | 20-25 | I-08 | 15-20 |
| I-09 | 25-30 | I-10 | 30-35 | I-11 | 30-35 |
| I-12 | 30-35 | I-13 | 30-35 | I-14 | 25-30 |
| I-15 | 35-40 | I-16 | 35-40 | I-17 | 30-35 |
| I-18 | 30-35 | I-19 | 25-30 | I-20 | 30-35 |
| I-21 | 30-35 | I-22 | 30-35 | I-23 | 30-35 |
| I-24 | 20-25 | I-25 | 10-15 | I-26 | 20-25 |
| I-27 | 25-30 | I-28 | 15-20 | SFE | 63 |
| F-01 | 60-65 | F-02 | 60-65 | F-03 | 55-60 |
| F-04 | 60-65 | F-05 | 60-65 | F-06 | 70-75 |

Note of Table 5:
the control is cell not treated with drug, and the data shown in the table are that the cell colony number of the control is 100%, and the inhibitory activity of the drug is expressed by the cell colony percentage of the drug-treated group and expressed as follows: Drug inhibitory activity = (cell colony number of drug-treated group/cell colony number of control group) × 100%.

The results show that each representative compound has good inhibitory effect on the formation of HMLE-Snail cell line spheroids, and has inhibitory activity stronger than docetaxel, SFN and PEITC and better than the non-aryl substituted congeneric compound, which proves that each representative compound can inhibit EMT path and has good potential therapeutic effect in inhibiting tumor cell metastasis.

Example 11. Detection of Inhibitory Activity of Representative Compound for High Metastasis Type Lung Cancer Cell Line NCI-H1975 and NCI-H1650 are two typical high metastasis type lung cancer cell lines. The therapeutic effect of the representative compound for the metastasis type lung cancers can be preliminarily assessed by detecting the inhibitory activity of the representative compound for the two cell lines. The lung cancer cell line was inoculated on 96-well cell culture plate in an amount of 6000 cells per well and cultured at 37° C. for 24 hours, and then treated solely with the compound added therein and cultured. Seventy-two hours later, MTT or CCK-8 method was used to detect the inhibitory activity of the compound for the two lung cancer cell lines. By the above steps, the inhibitory activity $IC_{50}$ values of SFN and the representative compound for the metastasis type lung cancer cell lines were detected respectively, and results are shown in Table 6.

TABLE 6

Inhibitory activity of part of representative compound for two high metastasis type lung cancer cell lines [72 hours, $IC_{50}$ (μM)]

| Cell line | Tissue | SFN | SFE | F-01 | F-03 | F-06 | I-01 | I-04 | I-08 | I-25 |
|---|---|---|---|---|---|---|---|---|---|---|
| NCI-H1975 | Lung | 20.3 | 8.8 | 6.9 | 5.8 | 17.2 | 3.1 | 0.09 | 0.17 | 0.25 |
| NCI-H1650 | Lung | 18.1 | 7.3 | 5.4 | 4.9 | 16.3 | 2.7 | 0.08 | 0.20 | 0.22 |

The results show that the representative compound has good inhibitory activity for the high metastasis type lung cancer cell lines. The representative compound would have better therapeutic effect on the lung cancer metastasis than SFN.

Example 12. Detection of Inhibitory Activity of Representative Compound for High Metastasis Type Colon Cancer Cell Lines SW620 and HCT116 are two typical high metastasis type colon cancer cell lines. The colon cancer cell line was inoculated on 96-well cell culture plate in an amount of 6000 cells per well and cultured at 37° C. for 24 hours, and then treated solely with the compound added therein and cultured. Seventy-two hours later, MTT or CCK-8 method was used to detect the inhibitory activity of the compound for the two high metastasis type colon cancer cell lines. By the above steps, the inhibitory activity $IC_{50}$ values of SFN and the representative compound for the high metastasis type colon cancer cell lines were detected respectively, and results are shown in the following Table 7.

TABLE 7

Inhibitory activity of representative compound for two high metastasis type colon cancer cell lines [72 hours, $IC_{50}$ (μM)]

| Cell line | Tissue | SFN | PEITC | SFE | F-01 | F-03 | F-06 | I-04 | I-06 | I-28 |
|---|---|---|---|---|---|---|---|---|---|---|
| SW620 | Colon | 15.1 | 10.2 | 4.7 | 4.1 | 3.3 | 17.8 | 0.09 | 0.15 | 0.19 |
| HCT116 | Colon | 13.2 | 8.4 | 3.9 | 3.5 | 2.9 | 15.6 | 0.07 | 0.10 | 0.15 |

The results show that the representative compound has good inhibitory activity for the high metastasis type colon cancer cell lines. The representative compound would have better therapeutic effect on the colon cancer metastasis than SFN and PEITC.

Example 13. Detection of Inhibitory Activity of Representative Compound for High Metastasis Type Lymphoma Cell Lines Jeko-1, Raji and U2932 are three typical high metastasis type lymphoma cell lines. The lymphoma cell line was inoculated on 96-well cell culture plate in an amount of 6000 cells per well and cultured at 37° C. for 24 hours, and then treated solely with the compound added therein and cultured. Seventy-two hours later, MTT or CCK-8 method was used to detect the inhibitory activity of the compound for the two high metastasis type lymphoma cell lines. By the above steps, the inhibitory activity $IC_{50}$ values of SFN, PEITC and the representative compound for the high metastasis type lymphoma cell lines were detected respectively, and inhibitory results of the representative compound for the high metastasis type lymphoma cell lines Jeko-1, Raji and U2932 are shown in the following Table 8. The results show that the compound of the present invention has inhibitory activity for the high metastasis type lymphoma cell lines far higher than the comparison compounds SFN and PEITC, and remarkably higher than the non-aryl substituted isothiocyanate compounds represented by SFE.

TABLE 8

Inhibitory activity of representative compound for two high metastasis type lymphoma cell lines [72 hours, $IC_{50}$ (μM)]

| Cell line | Tissue | SFN | PEITC | SFE | F-01 | F-03 | F-06 | I-04 | I-06 | I-25 |
|---|---|---|---|---|---|---|---|---|---|---|
| Jeko-1 | Lymph | 10.1 | 8.7 | 3.6 | 3.5 | 3.1 | 12.0 | 0.05 | 0.07 | 0.15 |
| Raji | Lymph | 11.0 | 9.3 | 4.0 | 3.7 | 3.2 | 13.5 | 0.06 | 0.10 | 0.18 |
| U2932 | Lymph | 13.4 | 11.7 | 5.9 | 5.2 | 4.9 | 14.7 | 0.09 | 0.17 | 0.25 |

Example 14. Detection of Inhibitory Activity of Representative Compound for High Metastasis Type Ovarian Cancer Cell Line HO-8910 and A2780 are two ovarian cancer cell lines with high metastasis potency, and are classic cell models for developing anti-ovarian cancer metastasis drugs. The two cell lines were inoculated on 96-well cell culture plate in an amount of 6000 cells per well and cultured at 37° C. for 24 hours, and then treated solely with the representative compound added therein and cultured. Seventy-two hours later, MTT or CCK-8 method was used to detect the inhibitory activity of the representative compound for the high metastasis type ovarian cancer cell lines. In addition, by the steps similar to the above steps, the inhibitory activity IC$_{50}$ values of SFN and the representative compound for the high metastasis type ovarian cancer cell lines were detected respectively, and results are shown in Table 9.

TABLE 9

Inhibitory activity of representative compound for two typical drug-resistant ovarian cancer cell lines [72 hours, IC$_{50}$ (μM)]

| Cell line | Tissue | SFN | PEITC | SFE | I-01 | I-25 | I-27 |
|---|---|---|---|---|---|---|---|
| HO-8910 | Ovary | 21.3 | 15.5 | 6.4 | 1.9 | 0.3 | 0.8 |
| A2780 | Ovary | 23.2 | 17.6 | 7.2 | 2.5 | 0.7 | 1.2 |

The results show that the representative compound has better inhibitory activity for the high metastasis type ovarian cancer cell lines and better potential therapeutic effect on the recurrence and metastasis of the ovarian cancer than SFN.

Figure 2:
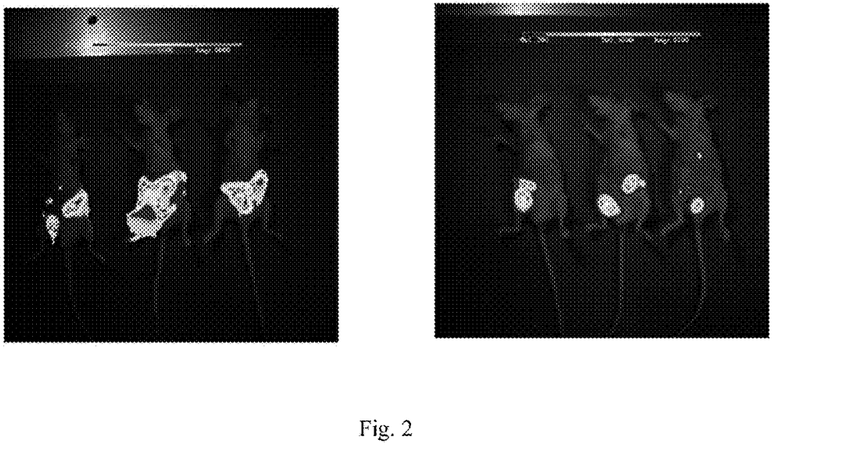
FIG. 2 is a figure showing therapeutic effect of the representative compound I-06 for ovarian cancer intraperitoneal metastasis model, observed with in vivo imaging apparatus, in which (a) control group (not treated with drug); (b) three weeks later after treated with the compound I-06 (80 mg/kg).

Example 15. Therapeutic Effect of Representative Compound for Ovarian Cancer Intraperitoneal Metastasis Animal Model The ovarian cancer intraperitoneal metastasis animal model is one of most classic animal models for studying anti-ovarian cancer metastasis drug. Sixty 5 to 6-week-old female nudemice with similar weight (BALB/c-nu/nu) were chosen. SK-OV3 (high metastasis type ovarian cancer cell line) stably expressing green fluorescence protein was screened, and prepared into a cell suspension of 2×10$^6$ cells/100 μl with serum-free PRMI1640 medium. 100 μl of the above cancer cell suspension was administrated to each nudemouse by intraperitoneal injection, and growth condition of cancer was observed at a fixed period, and the nudemice were continued to be fed. Five days later after the cancer implantation, the 60 female mice were divided into 10 groups randomly, six mice per group, intraperitoneal injection was performed once a day for 3 weeks to the control group (0.9% normal saline) and the drug-treated group (80 mg/kg of the representative compound) respectively, and cancer growth and metastasis conditions were observed with stereomicroscope at a fixed period. Three weeks later, the cancer was detected with a small animal in vivo imaging apparatus (Xenogen, School of Medicine, Shanghai Jiaotong University) and photos thereof were taken. Based on the inhibitory action of the representative compound on the intraperitoneal metastasis of ovarian cancer, the therapeutic effect of the representative compound on the ovarian cancer intraperitoneal metastasis animal model was assessed. Results are shown in Table 10. In the table, T represents the drug-treated group, and C represents the blank control group. T/C is (V/V$_0$ of compound-treated group)/(V/V$_0$ of blank control group) in which V represents the cancer volume of mouse on the day the detection was performed, and V$_0$ represents the cancer volume of mouse on the day the administration begun. The therapeutic effect of the representative compound I-06 on the ovarian cancer intraperitoneal metastasis model, i.e. the abdominal tumor pathological improvement effects after 3 weeks, is specifically shown in FIG. 2.

TABLE 10

Therapeutic effect of representative compound for ovarian cancer metastasis animal model

| Compound No. | Dose | T/C (%) | Mortality (within 30 days) |
|---|---|---|---|
| Control group | N/D | 100 | 2/6 |
| SFN | 80 mg/kg | 95 | 1/6 |
| PEITC | 80 mg/kg | 71 | 0/6 |
| Docetaxel | 20 mg/kg | 77 | 0/6 |
| I-04 | 80 mg/kg | 19 | 0/6 |
| I-08 | 80 mg/kg | 23 | 0/6 |
| I-17 | 80 mg/kg | 27 | 0/6 |
| I-27 | 80 mg/kg | 25 | 0/6 |
| SFE | 80 mg/kg | 42 | 0/6 |
| F-01 | 80 mg/kg | 37 | 0/6 |
| F-03 | 80 mg/kg | 35 | 0/6 |
| F-06 | 80 mg/kg | 80 | 1/6 |

The results show that the representative compound has good effect in inhibiting the intraperitoneal metastasis of malignant ovarian cancer. The representative compound has more excellent inhibitory activity for the intraperitoneal metastasis of malignant ovarian cancer than docetaxel, SFN and PEITC.

Example 16. Inhibitory Activity of Representative Compound for Other High Metastasis Type Cancer Cell Line The other type cancer cell lines with high metastasis potency were inoculated on 96-well cell culture plate in an amount of 6000 cells per well and cultured at 37° C. for 24 hours, and then treated solely with the compound added therein and cultured. Seventy-two hours later, MTT or CCK-8 method was used to detect the inhibitory activity IC$_{50}$ value of the compound for the high metastasis type cancer cell lines, and results are shown in Table 11.

TABLE 11

Inhibitory activity of representative compound for other high metastasis type cancer cell lines [72 hours, IC$_{50}$ (μM)]

| Cell line | Tissue | Type | SFN | SFE | I-01 | I-03 |
|---|---|---|---|---|---|---|
| Panc-1 | Pancreas | High metastasis type | 12.1 | 6.7 | 3.3 | 1.6 |
| KYSE-70 | Oesophagus | High metastasis type | 11.3 | 6.1 | 2.7 | 1.8 |
| Saos-2 | Bone and muscle | High metastasis type | 14.5 | 7.8 | 3.2 | 2.6 |
| 786-O | Kidney | High metastasis type | 10.2 | 5.4 | 1.0 | 1.3 |
| CaSki | Uterine neck | High metastasis type | 11.0 | 6.4 | 2.1 | 1.5 |

The results show that the representative compound has good inhibitory activity for each of the high metastasis type cancer cell lines. The representative compound has better potential therapeutic effect on the tumor metastasis than SFN.

What is claimed is:

1. An isothiocyanate compound of formula I:

I wherein R is selected from phenyl, a five- to six-membered mononuclear heteroaryl including 1-3 heteroatoms each independently selected from nitrogen, oxygen or sulfur, an eight- to ten-membered dinuclear aryl, an eight- to ten-membered dinuclear heteroaryl including 1-4 heteroatoms each independently selected from nitrogen, oxygen or sulfur, a ten- to fourteen-membered trinuclear aryl, or a ten- to fourteen-membered trinuclear heteroaryl including 1-4 heteroatoms each independently selected from nitrogen, oxygen or sulfur;

wherein R is unsubstituted, or is optionally substituted with one or more independently selected W substituents, wherein the W substituent is selected from halogen, $C_{1-4}$ alkoxy, $C_{1-4}$ haloalkyl, a five- to six-membered mononuclear heteroaryl including 1-3 heteroatoms, each independently selected from nitrogen, oxygen or sulfur, a four- to seven-membered heterocycloalkyl, including 1-3 heteroatoms, each independently selected from nitrogen, oxygen or sulfur, or an eight- to ten-membered dinuclear heteroaryl including 1-4 heteroatoms, each independently selected from nitrogen, oxygen or sulfur; and wherein n is 0, 1 or 2.

2. The isothiocyanate compound according to claim 1, wherein R is further selected from, benzofuryl, benzopyranyl, benzopyronyl, benzothienyl, benzothiazolyl, benzopyrazolyl, benzoimidazolyl, benzooxazolyl, carbazolyl, cinnolinyl, dibenzofuryl, dibenzothienyl, furyl, indolyl, imidazolyl, isoquinolyl, oxazolyl, quinolyl, quinazolinyl, quinoxalinyl, thienyl, tetrazolyl, thiazolyl, pyranyl, pyronyl, pyridyl, pyridazinyl, pyrazolyl, pyrimidyl, pyrazinyl, phenoxazinyl, phenothiazinyl, phenazinyl, purinyl, or a di- to tri-nuclear group optionally fused from the above mononuclear groups.

3. An isothiocyanate compound according to claim 1, wherein the compound is one of the following compounds:
 (1) (E)-((4-isothiocyanatobut-1-en-1-yl)sulfinyl)benzene
 (2) (E)-1-bromo-4-((4-isothiocyanatobut-1-en-1-yl)sulfinyl)benzene
 (3) (E)-1-chloro-4-((4-isothiocyanatobut-1-en-1-yl)sulfinyl)-2-(trifluoromethyl)benzene
 (4) (E)-1-((4-isothiocyanatobut-1-en-1-yl)sulfinyl)-3,5-bis(trifluoromethyl)benzene
 (5) (E)-1-((4-isothiocyanatobut-1-en-1-yl)sulfinyl)-3-methoxy-5-(trifluoromethyl)benzene
 (6) (E)-5-((4-isothiocyanatobut-1-en-1-yl)sulfinyl)-1,2,3-trimethoxybenzene
 (7) (E)-3-((4-isothiocyanatobut-1-en-1-yl)sulfinyl)-5-(trifluoromethyl)benzenesulfonamide
 (8) (E)-3-((4-isothiocyanatobut-1-en-1-yl)sulfinyl)-5-(trifluoromethyl)benzonitrile
 (9) (E)-4-(4-((4-isothiocyanatobut-1-en-1-yl)sulfinyl)phenyl)morpholine
 (10) (E)-6-((4-isothiocyanatobut-1-en-1-yl)sulfinyl)-1,2,3,4-tetrahydronaphthalene
 (11) (E)-2-((4-isothiocyanatobut-1-en-1-yl)sulfinyl)naphthalene
 (12) (E)-2-((4-isothiocyanatobut-1-en-1-yl)sulfinyl)anthracene
 (13) (E)-9-((4-isothiocyanatobut-1-en-1-yl)sulfinyl)-1H-phenalene
 (14) (E)-2-((4-isothiocyanatobut-1-en-1-yl)sulfinyl)-9H-fluorene
 (15) (E)-3-((4-isothiocyanatobut-1-en-1-yl)sulfinyl)pyridine
 (16) (E)-3-((4-isothiocyanatobut-1-en-1-yl)sulfinyl)-5-(trifluoromethyl)pyridine
 (17) (E)-6-((4-isothiocyanatobut-1-en-1-yl)sulfinyl)quinoline
 (18) (E)-6-((4-isothiocyanatobut-1-en-1-yl)sulfinyl)quinazoline
 (19) (E)-6-((4-isothiocyanatobut-1-en-1-yl)sulfinyl)-2H-chromen-2-one
 (20) (E)-2-((4-isothiocyanatobut-1-en-1-yl)sulfinyl)benzo[d]thiazole
 (21) (E)-2-((4-isothiocyanatobut-1-en-1-yl)sulfinyl)-5-(trifluoromethyl)benzo[d]thiazole
 (22) (E)-2-((4-isothiocyanatobut-1-en-1-yl)sulfinyl)-1H-benzo[d]imidazole
 (23) (E)-2-((4-isothiocyanatobut-1-en-1-yl)sulfinyl)-6-(trifluoromethyl)-1H-benzo[d]imidazole
 (24) (E)-2-((4-isothiocyanatobut-1-en-1-yl)sulfinyl)-6-methoxy-1H-benzo[d]imidazole
 (25) (E)-5-((4-isothiocyanatobut-1-en-1-yl)sulfinyl)-1-phenyl-1H-tetrazole
 (26) (E)-4-((4-isothiocyanatobut-1-en-1-yl)sulfinyl)-1,1'-biphenyl
 (27) (E)-1-((4-isothiocyanatobut-1-en-1-yl)sulfinyl)-4-phenoxybenzene
 (28) (E)-(4-((4-isothiocyanatobut-1-en-1-yl)sulfinyl)phenyl)(4-methoxyphenyl)sulfane.

4. An XPO1 protein inhibitor drug including an isothiocyanate compound according to claim 3 and a pharmaceutically acceptable carrier.

5. The XPO1 protein inhibitor drug according to claim 4, wherein the pharmaceutically acceptable carrier is an excipient, a filler, an adhesive, a wetter, a disintegrant, a surfactant, a lubricant, a dispersant, a pH regulator, a conservant, a chelating agent, a cosolvent or a stabilizer.

* * * * *